US012653833B2

(12) United States Patent
Dhuppad et al.

(10) Patent No.: US 12,653,833 B2
(45) Date of Patent: Jun. 16, 2026

(54) NASAL SPRAY COMPOSITION

(71) Applicant: Glenmark Specialty S.A., Neuchatel (CH)

(72) Inventors: Ulhas Dhuppad, Navi Mumbai (IN); Ashok Katkurwar, Nashik (IN); Rajesh Ankam, Nashik (IN); Pravinkumar Sharma, Nashik (IN)

(73) Assignee: GLENMARK SPECIALTY S.A., Neuchatel (CH)

( * ) Notice: Subject to any disclaimer, the term of this patent is extended or adjusted under 35 U.S.C. 154(b) by 0 days.

(21) Appl. No.: 18/955,763

(22) Filed: Nov. 21, 2024

(65) Prior Publication Data

US 2025/0161328 A1 May 22, 2025

(30) Foreign Application Priority Data

Nov. 21, 2023 (IN) .............................. 202321078834

(51) Int. Cl.

| | |
|---|---|
| *A01N 43/00* | (2006.01) |
| *A01N 43/46* | (2006.01) |
| *A61K 9/00* | (2006.01) |
| *A61K 31/335* | (2006.01) |
| *A61K 31/55* | (2006.01) |
| *A61K 31/58* | (2006.01) |
| *A61K 47/10* | (2017.01) |
| *A61K 47/18* | (2017.01) |
| *A61K 47/26* | (2006.01) |
| *A61K 47/38* | (2006.01) |
| *A61M 15/00* | (2006.01) |

(52) U.S. Cl.
CPC ............ *A61K 31/58* (2013.01); *A61K 9/0043* (2013.01); *A61K 31/335* (2013.01); *A61K 47/10* (2013.01); *A61K 47/183* (2013.01); *A61K 47/186* (2013.01); *A61K 47/26* (2013.01); *A61K 47/38* (2013.01); *A61M 15/009* (2013.01)

(58) Field of Classification Search
None
See application file for complete search history.

(56) References Cited

FOREIGN PATENT DOCUMENTS

| | | |
|---|---|---|
| AU | 2020397728 A1 | 6/2022 |
| CA | 3088490 A1 | 8/2019 |
| KR | 20130030606 A | 3/2013 |
| WO | 2014092346 A1 | 6/2014 |
| WO | 2015036902 A1 | 3/2015 |
| WO | 2019006173 A1 | 1/2019 |

OTHER PUBLICATIONS

International Search Report and Written Opinion Issued in PCT/IB2024/061643 on Feb. 7, 2025.
Ryaltris prescribing information, Aug. 29, 2023.

*Primary Examiner* — Layla Soroush
(74) *Attorney, Agent, or Firm* — Blank Rome LLP

(57) ABSTRACT

The present invention relates to a pharmaceutical composition in the form of an aqueous suspension suitable for nasal administration. The composition comprises mometasone furoate or a hydrate thereof, olopatadine or a pharmaceutically acceptable salt thereof (e.g., olopatadine hydrochloride), and a means for controlling clogging of an actuator and/or dip tube in a spray apparatus from which the composition is administered. The composition is suitable to provide consistent delivery, for example, for at least 5 days without clogging in the actuator or dip tube of a nasal spray device. The present invention also relates to a process of preparing the composition in the form of an aqueous suspension.

14 Claims, 1 Drawing Sheet

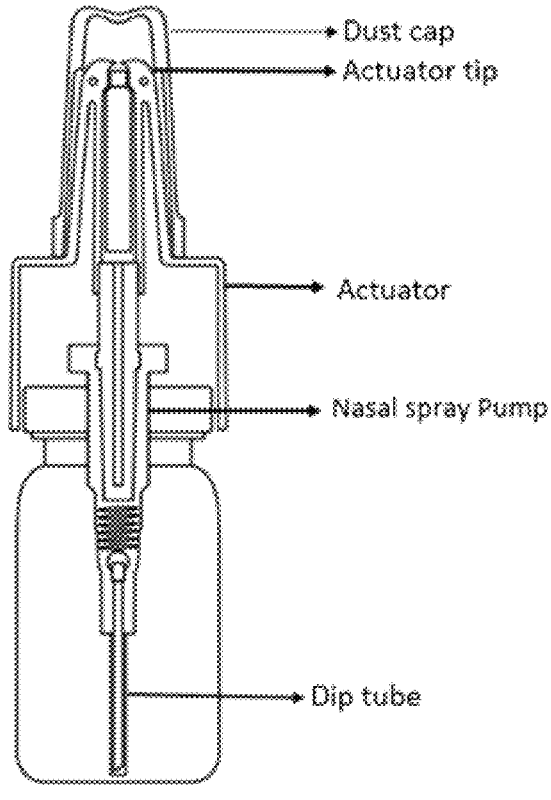

NASAL SPRAY COMPOSITION

RELATED APPLICATION

This application claims the benefit of Indian Provisional Patent Application No. 20/232,1078834 filed on Nov. 21, 2023, the entire disclosure of which is incorporated by reference herein.

FIELD OF THE INVENTION

The present invention relates to a pharmaceutical composition in the form of an aqueous suspension suitable for nasal administration. The composition comprises mometasone furoate or a hydrate thereof, olopatadine or a pharmaceutically acceptable salt thereof (e.g., olopatadine hydrochloride), and a means for controlling clogging of an actuator and/or dip tube in a spray device from which the composition is administered. The composition is suitable to provide consistent delivery, for example, for at least 30 days without clogging in the actuator or dip tube of a nasal spray device. The present invention also relates to a process of preparing the composition in the form of an aqueous suspension.

BACKGROUND OF THE INVENTION

Nasal spray devices for the delivery of an active ingredient to the nasal cavity, mostly the nasal mucosa, can be useful for the prophylaxis and/or treatment of certain diseases and disorders of the nasal cavity. Such devices are also capable of delivering a medicament to the systemic circulation via the turbinates and lymphoid tissues located at the back of the nasal cavity and to the central nervous system via the olfactory region at the top of the nasal cavity.

Nasal spray drug products contain therapeutically active ingredients dissolved or suspended in solutions or mixtures of excipients, such as, e.g., preservatives, viscosity modifiers, emulsifiers, buffering agents in non-pressurized dispensers that deliver a spray containing a metered dose of the active ingredient. The dose can be metered by the spray pump or may be pre-metered during manufacture. A nasal spray unit can be designed for unit dosing or can discharge up to several hundred metered sprays of formulation containing the drug substance.

The dose may be delivered by the integral pump components of the container closure system to the intra-nasal cavity by nasal spray for local and/or systemic effects.

The container closure system of these drug products comprises a container, a closure, an actuator and a pump. It may also include a protective packaging comprising a dust cap. Regardless of the design, the most crucial attributes of such nasal sprays are the reproducibility of dose, spray plume, spray content uniformity and droplet size distribution. These parameters are significant and can affect the delivery of drug to the site of administration and intended biological target.

A metered nasal spray composition comprising mometasone furoate and olopatadine hydrochloride is disclosed in International Publication No. WO 2015/036902. Although those compositions are stable, they may result in clogging of the actuator and/or dip tube that can impact consistent delivery of the suspension from the metered nasal spray.

To control such clogging problems associated with metered dose nasal spray devices, a patient information leaflet typically provides instructions to the patient to wipe the spray pump tip with a clean dry tissue or cloth and hold the spray pump unit and push the dust cap back on the spray pump tip of the bottle after use. However, if the patient doesn't follow the instructions properly, the patient may encounter inconsistent delivery due to clogging of the actuator and/or dip tube. Accordingly, such a patient instruction is typically not an effective solution to controls clogging problems associated with metered dose nasal spray devices.

There is a need for new methods to control clogging problems associated with compositions comprising mometasone furoate or a hydrate thereof and olopatadine hydrochloride delivered by metered dose nasal spray devices. The present invention addresses such needs.

SUMMARY OF THE INVENTION

In one aspect, the present invention is directed to a pharmaceutical composition comprising mometasone, an ester thereof (e.g., mometasone furoate), or a salt thereof and olopatadine or a salt thereof (e.g., olopatadine hydrochloride) and a means for controlling clogging associated with a nasal spray device (e.g., a metered dose nasal spray device). The means for controlling clogging can be a de-clogging agent. The pharmaceutical composition is suitable for a nasal spray device comprising an actuator and a dip tube through which the composition is to be delivered. The means for controlling clogging (such as by the inclusion of a de-clogging agent) avoids or minimizes clogging in the actuator and/or dip tube of the nasal spray device.

In one embodiment, the pharmaceutical composition may be used for the treatment of allergic rhinitis in a human subject.

The addition of a means for controlling clogging (e.g., a de-clogging agent) in the pharmaceutical composition achieves consistent dosing of the mometasone and olopatadine components and avoids clogging of a nasal spray actuator and/or dip tube.

In one embodiment, the composition comprises mometasone furoate, olopatadine hydrochloride, and a de-clogging agent.

In one embodiment, the pharmaceutical composition is an aqueous suspension comprising a hydrocolloid, wherein the mometasone (or an ester thereof, e.g., mometasone furoate, or a salt thereof) is present in particulate form and the olopatadine or a salt thereof (e.g., olopatadine hydrochloride) is present in dissolved form. In one embodiment, the pharmaceutical composition comprises an amount of a hydrocolloid such that the pharmaceutical composition has a viscosity of about 10 cps to about 200 cps, such as from about 20 cps to about 150 cps or from about 20 cps to about 120 cps. The pharmaceutical composition may comprise about 0.001% w/w to about 0.075% w/w mometasone, an ester thereof (e.g., mometasone furoate), or a salt thereof in particulate form, and about 0.5% w/w to about 0.8% w/w olopatadine or a salt thereof (e.g., olopatadine hydrochloride) in dissolved form.

In one embodiment, the pharmaceutical composition comprises about 0.001% w/w to about 0.075% w/w mometasone, an ester thereof (e.g., mometasone furoate), or a salt thereof in particulate form and about 0.5% w/w to about 0.8% w/w olopatadine or its salt (e.g., olopatadine hydrochloride) in dissolved for, and a means for controlling clogging of a nasal spray actuator and/or dip tube, such as a de-clogging agent.

In another embodiment, the pharmaceutical composition comprises about 0.025% w/w to about 0.05% w/w mometasone, an ester thereof (e.g., mometasone furoate), or a salt thereof in particulate form, about 0.5% w/w to about 0.8% w/w olopatadine or its salt (e.g., olopatadine hydrochloride), and about 0.05% w/w to about 5% w/w of a de-clogging agent.

In yet another embodiment, the pharmaceutical composition comprises about 0.025% w/w to about 0.05% w/w mometasone, an ester thereof (e.g., mometasone furoate), or a salt thereof in particulate form, about 0.6% w/w to about 0.7% w/w olopatadine or its salt (e.g., olopatadine hydrochloride), and about 0.05% w/w to about 5% w/w of a de-clogging agent.

In yet another embodiment, the pharmaceutical composition comprises about 0.025% w/w to about 0.05% w/w mometasone, an ester thereof (e.g., mometasone furoate), or a salt thereof in particulate form, about 0.6% w/w to about 0.7% w/w olopatadine or its salt (e.g., olopatadine hydrochloride), and about 0.1% w/w to about 5% w/w of a de-clogging agent.

In yet another embodiment, the pharmaceutical composition comprises about 0.025% w/w to about 0.05% w/w mometasone furoate in particulate form, about 0.6% w/w to about 0.7% w/w olopatadine hydrochloride, and about 0.1% w/w to about 3% w/w of a de-clogging agent.

In another embodiment, the pharmaceutical composition comprises mometasone furoate in an amount of about 0.025% w/w in particulate form, olopatadine hydrochloride in an amount of about 0.665% w/w in dissolved form, and a means for controlling clogging at an actuator from which the composition is delivered to facilitate consistent delivery of the composition.

In yet another embodiment, any of the pharmaceutical compositions described herein is an aqueous suspension for nasal administration to a human comprising about 0.025% w/w mometasone furoate, about 0.665% w/w olopatadine hydrochloride and about 0.05% w/w to about 5% w/w of glycerol.

In yet another embodiment, the pharmaceutical composition described herein comprises glycerol in an amount of about 0.05% w/w to about 3% w/w, about 0.05% w/w to about 2% w/w, or about 0.05% w/w to about 1% w/w.

In yet another embodiment, the pharmaceutical composition described herein comprises glycerol in an amount of about 0.075% w/w to about 3% w/w, about 0.075% w/w to about 2% w/w, or about 0.075% w/w to about 1% w/w.

In yet another embodiment, the pharmaceutical composition described herein comprises glycerol in an amount of about 0.05% w/w, about 0.06% w/w, about 0.07% w/w, about 0.075% w/w, about 0.08% w/w, about 0.085% w/w, about 0.09% w/w, about 0.095% w/w, about 0.1% w/w, about 0.125% w/w, about 0.15% w/w, about 0.17% w/w, about 0.18% w/w, about 0.19% w/w, about 0.2% w/w, about 0.225% w/w, about 0.25% w/w, about 0.27% w/w, about 0.28% w/w, about 0.3% w/w, about 0.4% w/w, about 0.5% w/w, about 1% w/w, about 2% w/w, or about 3% w/w.

In another embodiment, the dispensing device (such as a nasal spray actuator and a pump) dispenses about 100 μl of the pharmaceutical composition per actuation, wherein a single actuation dispenses about 665 μg of olopatadine hydrochloride and about 25 μg or about 50 μg of mometasone furoate (preferably 25 μg mometasone furoate).

In additional embodiments, the dispensing device may include a container, a cap, and a dispenser head which can include a pump, a dip tube, an actuator, a dispensing channel and a dispensing orifice. The pump is designed to dispense the pharmaceutical composition through the dip tube into the pump through the actuator fitted with the dispensing orifice. The pharmaceutical composition is released in the form of a uniform spray. Pump can operate in tandem with the actuator which allow for easy opening and closing of the pump and provide for a desired spray characteristic. Actuators include, but are not limited to, spray actuators, foam actuators, solid-stream actuators, and special actuators. The dispensing device delivers a nasal spray in a uniform dose of, for example, mometasone (e.g., as mometasone furoate) and olopatadine (e.g., as olopatadine hydrochloride), where the dose is dispensed every time the dispensing device is actuated by a user.

The dispensing device may require priming, for example, for about 2-6 actuations, to consistently dispense the composition. The device may be primed by releasing 6 sprays or until a fine mist appears. The droplet size of the nasal spray may be controlled by the size of the dispensing orifice of the container. The dispensing orifice size may also influence characteristics of the spray pattern.

BRIEF DESCRIPTION OF THE DRAWING

The present invention is better understood with reference to the following description taken in combination with the drawing. For the purpose of illustration, there are shown in the drawing certain embodiments of the present invention. It should be understood, however, that the invention is not limited to the precise arrangements, dimensions, and instruments shown:

FIG. 1 illustrates a nasal spray device comprising a container, dip tube, nasal spray pump, actuator, actuator tip and dust cap and pharmaceutical composition of the present invention.

DETAILED DESCRIPTION OF THE INVENTION

In a nasal spray product comprising a suspension formulation, a patient information leaflet typically provides instructions to the patient to wipe the spray pump tip with a clean dry tissue or cloth and hold the spray pump unit and push the dust cap back on the spray pump tip of the bottle after use. However, typically patients forget to wipe the tip actuator, or fit the dust cap improperly which may result in clogging of the actuator and/or dip-tube. Such clogging further leads to lack of reproducibility of dose uniformity, spray plume, spray content uniformity and droplet size distribution. These problems then cause improper delivery of the drug to the nasal cavity.

The present inventors have surprisingly and unexpectedly found that addition of a de-clogging agent can substantially control the clogging in the actuator and/or dip tube.

In one aspect, the present invention is directed to a pharmaceutical composition for nasal administration to a human subject for the treatment of rhinitis, the composition comprising mometasone, an ester thereof (e.g., mometasone furoate), or a salt thereof and olopatadine or its salt (e.g., olopatadine hydrochloride) and a means for controlling clogging associated with a nasal spray device (e.g., a metered dose nasal spray device).

In another aspect, the present invention is directed to a dispensing device containing a pharmaceutical composition comprising mometasone, an ester thereof (e.g., mometasone furoate), or a salt thereof and olopatadine or its salt (e.g., olopatadine hydrochloride) and a means for controlling clogging problems associated with a metered dose nasal spray device.

In one embodiment, the means for controlling clogging is a de-clogging agent. Suitable de-clogging agents include, but are not limited to, sugar alcohols (polyols), polyethers, or any combination thereof.

In one embodiment, the de-clogging agent is glycerol (or glycerin), sorbitol, mannitol, propylene glycol, polyethylene glycol, or any combination of any of the foregoing.

In one embodiment, the de-clogging agent is present in the pharmaceutical composition in a sufficient amount to controls the clogging of actuator, such as, for example, during storage at 25° C. and 60% relative humidity (RH), or 30° C. and 65% RH, or 30° C. and 75% RH, or 40° C. and 75% RH for 1, 2, 3, 4, 5, or 6 months. In another embodiment, the declogging agent is present in the pharmaceutical composition in an amount of about 0.01% w/w to about 5% w/w, based upon the total weight of pharmaceutical composition. In yet another embodiment, the declogging agent is present in the pharmaceutical composition in an amount of about 0.05% w/w to about 5% w/w (such as from about 0.05% to about 2% w/w), based upon the total weight of pharmaceutical composition.

Such nasal spray compositions provide the advantage that patients are not required to wipe the tip of the actuator after every use and no clogging is observed even if the cap is not fitted properly onto the dispensing device, e.g., for up to 30 days.

Another embodiment is a pharmaceutical composition comprising mometasone furoate in an amount of about 0.025% w/w in particulate form, olopatadine hydrochloride in an amount of about 0.665% w/w in dissolved form, and a means for controlling clogging at an actuator from which the composition is delivered to facilitate consistent delivery of the composition.

In another embodiment, the addition of a de-clogging agent in a pharmaceutical composition (for example, an aqueous suspension composition) comprising mometasone furoate and olopatadine hydrochloride controls (or avoid, reduce or repress) the clogging of a nasal spray actuator and/or dip tube (through which the pharmaceutical composition is delivered) for at least 5 days (e.g., when stored at 25±2° C. and 60%±5% relative humidity), when the dispensing device remains open without putting a dust cap on it.

In one embodiment of any of the pharmaceutical compositions described herein, the pharmaceutical composition is stored under standard conditions (at 25±2° C. and 60%±5% relative humidity).

In another embodiment, the addition of a de-clogging agent in a pharmaceutical composition (for example, an aqueous suspension composition) comprising mometasone furoate and olopatadine hydrochloride controls (or avoid, reduce or repress) the clogging of a nasal spray actuator and/or dip tube for at least about 10 days, when the dispensing device remains open without putting a dust cap on it.

In one embodiment, the addition of a de-clogging agent in a pharmaceutical composition (for example, an aqueous suspension composition) comprising mometasone furoate and olopatadine hydrochloride controls (or avoid, reduce or repress) the clogging of a nasal spray actuator and/or dip tube for at least about 15 days, when the dispensing device remains open without putting a dust cap on it.

One embodiment is a pharmaceutical composition (for example, an aqueous suspension composition) comprising mometasone furoate, olopatadine hydrochloride, and a sufficient amount of a de-clogging agent to controls (or reduce or repress) the clogging of a nasal spray actuator and/or dip tube (for example, for at least about 30 days), when the dispensing device remains open without putting a dust cap on it.

In another aspect, the addition of a de-clogging agent in a pharmaceutical composition (for example, an aqueous suspension composition) comprising mometasone furoate and olopatadine hydrochloride controls (or avoid, reduce or repress) the clogging of a nasal spray actuator and/or dip tube for at least about 5 days, such as for about 10 days, for about 15 days or for about 30 days, when the dispensing device remains open without putting a dust cap on it.

In one embodiment, the addition of a de-clogging agent in an aqueous suspension composition controls (or avoid, reduce or repress) the clogging of nasal spray actuator and/or dip tube for about 15 days, for about 20 days, for about 25 days, for about 30 days when the dispensing device remains open without putting a dust cap on it.

In another embodiment, the addition of a de-clogging agent in an aqueous suspension composition controls the clogging of a nasal spray actuator and/or dip tube for about 5 days to about 30 days, for about 5 days to about 25 days, for about 5 days to about 20 days, for about 5 days to about 15 days, for about 5 days to about 10 days when the dispensing device remains open without putting a dust cap on it.

In another embodiment, the addition of a de-clogging agent in an aqueous suspension composition controls the clogging of a nasal spray actuator and/or dip tube for about 8 days, for about 12 days, for about 16 days, for about 22 days, for about 28 days when the dispensing device remains open without putting a dust cap on it.

In another embodiment, the addition of a de-clogging agent in an aqueous suspension composition controls the clogging of a nasal spray actuator and/or dip tube for about 7 days to about 17 days, for about 10 days to about 20 days, for about 15 days to about 20 days, for about 15 days to about 25 days, for about 15 days to about 30 days, when the dispensing device remains open without putting a dust cap on it.

In another embodiment, the addition of a de-clogging agent in an aqueous suspension composition controls the clogging of a nasal spray actuator and/or dip tube for about 10 days to about 30 days, for about 10 days to about 25 days when the dispensing device remains open without putting a dust cap on it.

In one embodiment of any of the pharmaceutical compositions described herein, the composition is an aqueous suspension comprising a hydrocolloid, mometasone, an ester thereof (e.g., mometasone furoate), or a salt thereof present in particulate form and olopatadine or a salt thereof (e.g., olopatadine hydrochloride) in dissolved form, and a de-clogging agent.

In one embodiment of any of the pharmaceutical compositions described herein, the composition comprises about 0.001% w/w to about 0.075% w/w of mometasone, an ester thereof (e.g., mometasone furoate), or a salt thereof in particulate form, about 0.5% w/w to about 0.8% w/w olopatadine or its salt (e.g., olopatadine hydrochloride) in dissolved form, and about 0.05% w/w to about 5% w/w of a de-clogging agent.

In one embodiment of any of the pharmaceutical compositions described herein, the composition comprises about 0.025% w/w to about 0.05% w/w mometasone, an ester thereof (e.g., mometasone furoate), or a salt thereof in particulate form; and about 0.5% w/w to about 0.8% w/w olopatadine or its salt (e.g., olopatadine hydrochloride). In this embodiment, the pharmaceutical composition may further comprise a hydrocolloid and about 0.05% w/w to about 5% w/w of a de-clogging agent.

In one embodiment of any of the pharmaceutical compositions described herein, the composition comprises about 0.025% w/w to about 0.05% w/w mometasone, an ester thereof (e.g., mometasone furoate), or a salt thereof in particulate form; and about 0.5% w/w to about 0.8% w/w olopatadine or its salt (e.g., olopatadine hydrochloride). In this embodiment, the pharmaceutical composition may further comprise a hydrocolloid and about 0.1% w/w to about 5% w/w of a de-clogging agent.

In one embodiment of any of the pharmaceutical compositions described herein, the composition comprises (a) about 0.025% w/w to about 0.05% w/w mometasone furoate in particulate form, (b) about 0.5% w/w to about 0.8% w/w olopatadine hydrochloride, and (c) about 0.1% w/w to about 5% w/w of a de-clogging agent. The pharmaceutical composition may further comprise a hydrocolloid.

Another embodiment is a pharmaceutical composition suitable for a nasal spray device comprising an actuator and a dip tube through which the composition is delivered, where (a) the composition is in the form of an aqueous suspension suitable for nasal administration, and (b) the composition comprises mometasone furoate (e.g., in an amount of about 0.025% w/w in particulate form), olopatadine or a pharmaceutically acceptable salt thereof (e.g., olopatadine hydrochloride in an amount of about 0.665% w/w in dissolved form), and an amount of a de-clogging agent sufficient to controls clogging at the actuator and dip tube from which the composition is delivered to facilitate consistent delivery of the composition. The de-clogging agent can be any such agent described herein. In one embodiment, the de-clogging agent is selected from glycerol, sorbitol, mannitol, propylene glycol, polyethylene glycol and any combination of any of the foregoing. In one preferred embodiment, the de-clogging agent is glycerol. In one embodiment, the glycerol is present in an amount of about 0.05% w/w to about 5% w/w. In another embodiment, the glycerol is present in an amount of about 0.05% w/w to about 1% w/w.

Yet another embodiment is a method of delivering a pharmaceutical composition comprising mometasone furoate and olopatadine hydrochloride to a patient in need thereof through an actuator and dip tube of a nasal spray device while decreasing clogging of the actuator or dip tube, the method comprising intranasally administering the pharmaceutical composition through the actuator and dip tube of the nasal spray device to the patient, where the pharmaceutical composition is in the form of an aqueous suspension suitable for nasal administration, and (b) the composition comprises mometasone furoate (e.g., in an amount of about 0.025% w/w in particulate form), olopatadine or a pharmaceutically acceptable salt thereof (e.g., olopatadine hydrochloride in an amount of about 0.665% w/w in dissolved form), and a means for controlling clogging at the actuator and dip tube from which the composition is delivered to facilitate consistent delivery of the composition. In one embodiment, the patient suffers from allergic rhinitis, such as seasonal allergic rhinitis or perennial allergic rhinitis. In one embodiment, the de-clogging agent is selected from glycerol, sorbitol, mannitol, propylene glycol, polyethylene glycol and any combination of any of the foregoing. In one preferred embodiment, the de-clogging agent is glycerol. In one embodiment, the glycerol is present in an amount of about 0.05% w/w to about 5% w/w. In another embodiment, the glycerol is present in an amount of about 0.05% w/w to about 1% w/w.

In yet another embodiment, the nasal spray device or dispensing device may include a container, a cap, and a dispenser head which can include a pump, a dip tube, an actuator, a dispensing channel and a dispensing orifice as shown in FIG. 1. The pump is designed to dispense the pharmaceutical composition through the dip tube into the pump through the actuator fitted with the dispensing orifice. The pharmaceutical composition is released in the form of a uniform spray. The pump can operate in tandem with the actuator which allows for easy opening and closing of the pump and provides for a desired spray characteristic. Actuators include, but are not limited to, spray actuators, foam actuators, solid-stream actuators, and special actuators. The container of the nasal spray device can be a round or oval; preferably, the container is round. The container may have a conically shaped internal bottom or flat bottom. A cap may or may not be included. The dispensing device delivers a nasal spray in a uniform dose of, for example, mometasone (e.g., as mometasone furoate) and olopatadine (e.g., as olopatadine hydrochloride), where the dose is dispensed every time the dispensing device is actuated by a user.

As further detailed below, in certain embodiments, the dispensing device is adequate to dispense about 100 µl of a pharmaceutical composition per actuation, wherein a single actuation dispenses about 665 µg of olopatadine hydrochloride and about 25 µg or about 50 µg of mometasone furoate, preferably 25 µg mometasone furoate.

Definitions

The singular forms "a," "an," and, "the" include plural references unless the context clearly dictates otherwise. Thus, for example, reference to a compound refers to one or more compounds or at least one compound. As such, the terms "a" (or "an"), "one or more," and "at least one" can be used interchangeably herein.

As used herein, the term "about" when referring to a number or a numerical range means that the number or numerical range referred to is an approximation within experimental variability (or within statistical experimental error), and the number or numerical range may vary from, for example, between 1% and 15% of the stated number or numerical range.

The term "effective amount" when used in connection with an active ingredient denotes an amount of the active ingredient that, when administered to a subject for treating rhinitis, produces an intended therapeutic benefit in a subject. The term "active ingredient" (used interchangeably with "active" or "active substance" or "drug") as used herein includes mometasone (or its ester, such as mometasone furoate) or its salt and olopatadine or its salt (such as olopatadine hydrochloride). The effective amount of mometasone (or its ester, such as mometasone furoate) or its salt can range from about 0.01 mg to about 10 mg, preferably from about 0.02 mg to about 5 mg, or more preferably from about 0.02 mg to about 3 mg. The effective amount of olopatadine or its salt (such as olopatadine hydrochloride) can range from about 0.05 mg to about 20 mg, preferably from about 0.1 mg to about 15 mg or more preferably from about 0.1 mg to about 10 mg.

As used herein, the term "α-hydroxy olopatadine" of olopatadine refers to "(Z)-2-{11-[3-(Dimethylamino)propylidene]-6,11-dihydrodibenz[b,e]oxepin-2-yl}-2-hydroxyacetic acid".

As used herein, the term "Olopatadine E-Isomer" refers to "11-[(E)-3-(Dimethylamino)propylidene]-6,11-dihydrodibenz[b,e]oxepin-2-acetic acid".

As used herein, the term "Olopatadine carbaldehyde (z) isomer" refers to "(Z)-11-(3-(dimethylamino)propylidene)-6,11-dihydrodibenzo[b,e]oxepine-2-carbaldehyde, hydrochloride".

As used herein, the term "Olopatadine Related Compound B" refers to "(Z)-3-{2-(Carboxymethyl)dibenzo[b,e]oxepin-11(6H)-ylidene}-N,N-dimethylpropan-1-amine oxide".

As used herein, the term "8-DM" of mometasone refers to "(9β, 11β-epoxy-17α, 21-dihydroxy-16α-methyl pregna-1, 4-dience-3,20-dione)".

As used herein, the term "DMC" of mometasone refers to "(21-chloro-9β, 11β-epoxy, 17α,-hydroxyl-16α-methyl pregna-1,4-dien-3,20-dione)".

As used herein, the term "DMCF" of mometasone refers to "(21-chloro-9β,11β-epoxy-16α-methyl-3,20-dioxo pregna-1,4-dien-17ylfuran-2-carboxylate)".

In an aspect of this invention, for daily administration by the nasal route, the effective amount of mometasone (or its ester, such as mometasone furoate) or its salt can range from about 10 μg to about 500 μg, preferably from about 20 μg to about 400 μg, and the effective amount of olopatadine or its salt (such as olopatadine hydrochloride) can range from about 50 μg to about 7000 μg, preferably from about 100 μg to about 5400 μg.

By "salt" or "pharmaceutically acceptable salt", it is meant those salts which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include, for example, hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include, for example, sodium, calcium, potassium and magnesium salts.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made By "pharmaceutically acceptable excipient", it is meant any of the components of a pharmaceutical composition other than the active ingredients which are approved by regulatory authorities or are generally regarded as safe for human or animal use.

As used herein, the term "average particle size" (or synonymously, "mean particle size") refers to the distribution of particles, wherein about 50 volume percent of all the particles measured have a size less than the defined average particle size value and about 50 volume percent of all particles measured have a particle size greater than the defined average particle size value. This can be identified by the term "$D_{50}$" or "$d_{(0.5)}$". The average particle size can be measured using various techniques such as, e.g., microscopy, laser diffraction, photon correlation spectroscopy (PCS) and Coulter's principle.

As used herein, the term "$D_{10}$" refers to the distribution of particles wherein about 10 volume percent of all the particles measured have a size less than the defined particle size value. This can be identified by the term "d (0.1)" as well. Similarly, as used herein, the term "$D_{80}$" refers to the distribution of particles wherein about 80 volume percent of all the particles measured have a size less than the defined particle size value. This can be identified by the term "d (0.8)" as well. On similar lines, as used herein, the term "$D_{90}$" refers to the distribution of particles wherein about 90 volume percent of all the particles measured have a size less than the defined particle size value. This can be identified by the term "d (0.9)" as well.

As used herein, the term "hydrocolloid" refers to a colloid system wherein hydrophilic colloid particles (e.g., hydrophilic polymers) are dispersed in water. The hydrocolloid system can exist in gel state or sol (liquid) state. In suspension compositions, the hydrocolloid functions as thickening, stabilizing and suspending agents. Non-limiting examples of hydrocolloid include cellulose derivatives (such as carboxymethyl cellulose sodium), xanthan gum, gum arabic, guar gum, locust bean gum, alginate, starch, agar-agar, carrageenan, gelatin, a mixture of microcrystalline cellulose & sodium carboxymethyl cellulose, or any combination of any of the foregoing. Preferably, the hydrocolloid includes xanthan gum or carboxymethyl cellulose sodium.

Hydrocolloids comprising a mixture of microcrystalline cellulose & carboxymethyl cellulose sodium can be a colloidal, water dispersible, spray-dried blend of microcrystalline cellulose and carboxymethylcellulose sodium or co-processed microcrystalline cellulose & carboxymethyl cellulose sodium or simple physical mixture of microcrystalline cellulose and carboxymethylcellulose sodium. A mixture of microcrystalline cellulose and carboxymethyl cellulose sodium, can be Avicel RC-591® (available from FMC Biopolymer, Philadelphia, Pa.) which contains 8.3% w/w to 13.8% w/w carboxymethylcellulose sodium.

Some embodiments of the present invention provide compositions comprising carboxymethylcellulose sodium. In some embodiments, the compositions comprise at least about 0.1% w/w carboxymethylcellulose sodium. In some embodiments, the compositions comprise about 0.1% w/w to about 3% w/w of carboxymethylcellulose sodium. In some embodiments, the compositions comprise from about 0.6%/w/w to about 2% w/w of carboxymethylcellulose sodium. In some embodiments, the compositions comprise from about 0.5% w/w to about 1.5% w/w carboxymethylcellulose sodium. In some embodiments, the compositions comprise about 0.5% w/w to about 1% w/w carboxymethylcellulose sodium. In some embodiments, the compositions comprise about 0.5% w/w to about 0.75% w/w carboxymethylcellulose sodium. In some embodiments, the compositions comprise about 0.67% w/w carboxymethylcellulose sodium. In some embodiments, the compositions comprise about 0.68% w/w carboxymethylcellulose sodium. In some embodiments, the compositions comprise about 0.9% w/w carboxymethylcellulose sodium. In some embodiments, the compositions comprise 1% w/w carboxymethylcellulose sodium. In some embodiments, the compositions comprise about 0.7% w/w carboxymethylcellulose sodium. In some embodiments, the compositions comprise 0.6656% w/w carboxymethylcellulose sodium.

The term "de-clogging agent" refers to an agent which controls or prevents or reduces or minimizes the clogging of the nasal spray actuator and/or dip tube. Non-limiting examples of de-clogging agent include glycerol (or glycerin), sorbitol, mannitol, propylene glycol, polyethylene glycol and mixtures thereof.

The term "controls clogging" means to prevent or avoid or reduce or minimize clogging of the nasal spray actuator and/or dip tube.

The term "consistent delivery" refers to a spray wherein each spray comprises, e.g., about 25 μg of mometasone furoate and about 665 μg of olopatadine hydrochloride with the desired in-vitro parameters, such as spray pattern, spray content uniformity, and droplet size distribution.

The terms "formulation" and "composition" are used interchangeably and refer to a mixture of at least one compound, element, or molecule. In some aspects the terms "formulation" and "composition" may be used to refer to a mixture of one or more active agents with one or more pharmaceutically acceptable excipients.

The pharmaceutical compositions for nasal administration to a human described herein may comprise about 0.001% w/w to about 0.075% w/w mometasone, an ester thereof (e.g., mometasone furoate), or a salt thereof, about 0.5% w/w to about 0.8% w/w olopatadine or its salt (e.g., olopatadine hydrochloride) and a de-clogging agent.

The pharmaceutical compositions described herein may be in the form of a solution or a suspension. In one preferred embodiment, the composition is in the form of a suspension (such as a single phase suspension), wherein mometasone, an ester thereof (e.g., mometasone furoate), or a salt thereof is present in particulate form and olopatadine or its salt (e.g., olopatadine hydrochloride) is present in dissolved form.

The compositions described herein preferably also include a hydrocolloid. In one embodiment, the composition is a suspension and includes a hydrocolloid in an amount of about 0.3% w/w to about 5% w/w to prevent phase separation (i.e., separation of the particles and solution) after 3 or 6 months of storage at 25±2° C. and 60%±5% relative humidity (RH) or at 40±2° C. and 75%±5% RH. In one embodiment, the aqueous pharmaceutical composition is a single phase suspension which remains a single phase suspension after 3 or 6 months of storage at 25±2° C. and 60%±5% RH or at 40±2° C. and 75%±5% RH.

In another embodiment, any of the pharmaceutical compositions described herein is an aqueous suspension for nasal administration to a human, wherein the composition comprises about 0.025% w/w to about 0.05% w/w mometasone, an ester thereof (e.g., mometasone furoate), or a salt thereof, about 0.6% w/w to about 0.7% w/w olopatadine or its salt (e.g., olopatadine hydrochloride), about 0.3% w/w to about 3% w/w hydrocolloid, and about 0.05% w/w to about 5% w/w de-clogging agent.

In another embodiment, any of the pharmaceutical compositions described herein is an aqueous suspension for nasal administration to a human, wherein the composition comprises about 0.025% w/w to about 0.05% w/w mometasone, an ester thereof (e.g., mometasone furoate), or a salt thereof, about 0.6% w/w to about 0.7% w/w olopatadine or its salt (e.g., olopatadine hydrochloride), about 0.3% w/w to about 3% w/w hydrocolloid, and about 0.1% w/w to about 5% w/w de-clogging agent.

In yet another embodiment, any of the pharmaceutical compositions described herein is an aqueous suspension for nasal administration to a human, wherein the composition comprises about 0.025% w/w to about 0.05% w/w mometasone furoate, about 0.6% w/w to about 0.7% w/w olopatadine hydrochloride, about 0.3% w/w to about 2% w/w hydrocolloid selected from carboxymethylcellulose sodium and xanthan gum, and about 0.05% w/w to about 5% w/w de-clogging agent, such as, e.g., glycerol (or glycerin), sorbitol, mannitol, propylene glycol, polyethylene glycol and any combination thereof.

In yet another embodiment, any of the pharmaceutical compositions described herein is an aqueous suspension for nasal administration to a human, wherein the composition comprises about 0.025% w/w to about 0.05% w/w mometasone furoate, about 0.6% w/w to about 0.7% w/w olopatadine hydrochloride, about 0.3% w/w to about 2% w/w hydrocolloid selected from carboxymethylcellulose sodium and xanthan gum, and about 0.1% w/w to about 5% w/w of de-clogging agent, such as, e.g., glycerol (or glycerin), sorbitol, mannitol, propylene glycol, polyethylene glycol and any combination thereof.

In yet another embodiment, any of the pharmaceutical compositions described herein is an aqueous suspension for nasal administration to a human, wherein the composition comprises about 0.025% w/w mometasone furoate, about 0.665% w/w olopatadine hydrochloride, at least about 0.3% w/w hydrocolloid selected from carboxymethylcellulose sodium and xanthan gum and about 0.1% w/w to about 3% w/w of de-clogging agent, such as, e.g., glycerol (or glycerin), sorbitol, mannitol, propylene glycol, polyethylene glycol and any combination thereof.

In yet another embodiment, any of the pharmaceutical compositions described herein is an aqueous suspension for nasal administration to a human, comprising about 0.025% w/w to about 0.05% w/w mometasone furoate, about 0.6% w/w to about 0.7% w/w olopatadine hydrochloride and a de-clogging agent such as, e.g., glycerol (or glycerin), sorbitol, mannitol, propylene glycol, polyethylene glycol and any combination thereof. The de-clogging agent may be present at a concentration of at least about 0.05% w/w, such as between about 0.1% w/w to about 3% w/w of the composition.

In yet another embodiment, any of the pharmaceutical compositions described herein is an aqueous suspension for nasal administration to a human, comprising about 0.025% w/w to about 0.05% w/w mometasone furoate, about 0.6% w/w to about 0.7% w/w olopatadine hydrochloride and a de-clogging agent such as, e.g., glycerol (or glycerin), sorbitol, mannitol, propylene glycol, polyethylene glycol and any combination thereof. The de-clogging agent may be present at a concentration of at least about 0.05% w/w or at least about 0.1% w/w of the composition.

In yet another embodiment, any of the pharmaceutical compositions described herein is an aqueous suspension for nasal administration to a human, comprising about 0.025% w/w to about 0.05% w/w mometasone furoate, about 0.6% w/w to about 0.7% w/w olopatadine hydrochloride and a de-clogging agent such as, e.g., glycerol (or glycerin), sorbitol, mannitol, propylene glycol, polyethylene glycol and any combination thereof. The de-clogging agent may be present at a concentration of about 0.05% w/w, about 0.1% w/w, about 0.2% w/w, about 0.3% w/w, about 0.4% w/w, about 0.5% w/w, about 0.6% w/w, about 0.8% w/w, about 1% w/w, about 1.2% w/w, about 1.3% w/w, about 1.5% w/w, about 2% w/w, about 2.5% w/w, about 3% w/w, about 3.5% w/w, about 4% w/w, about 4.5% w/w or about 5% w/w of the composition.

In another embodiment, any of the pharmaceutical compositions described herein is an aqueous suspension for nasal administration to a human, comprising about 0.025% w/w to about 0.05% w/w mometasone furoate, about 0.6% w/w to about 0.7% w/w olopatadine hydrochloride and a de-clogging agent such as, e.g., glycerol (or glycerin), sorbitol, mannitol, propylene glycol, polyethylene glycol and any combination thereof. The de-clogging agent may be present at a concentration of about 0.05% w/w to about 1% w/w, about 0.1% w/w to about 1% w/w, about 1% w/w to about 1.5% w/w, about 1.5% w/w to about 2.5% w/w, about 2.5% w/w to about 3% w/w, about 3% w/w to about 3.5% w/w, about 3.5% w/w to about 4% w/w, or about 4% w/w to about 5% w/w of the composition.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.05% w/w to about 5% w/w of a de-clogging agent.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.1% w/w to about 5% w/w of a de-clogging agent.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.1% w/w to about 3% w/w of a de-clogging agent.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.1% w/w to about 1% w/w of a de-clogging agent.

In yet another embodiment, any of the pharmaceutical compositions described herein is an aqueous suspension for nasal administration to a human, comprising about 0.025% w/w mometasone furoate, about 0.665% w/w of olopatadine hydrochloride and a de-clogging agent in an amount at a concentration of about 0.05% w/w or about 0.1% w/w, about 0.2% w/w, about 0.3% w/w, about 0.4% w/w, about 0.5% w/w, about 0.6% w/w, about 0.8% w/w, about 1% w/w, about 1.2% w/w, about 1.3% w/w, about 1.5% w/w, about 2% w/w, about 2.5% w/w, about 3% w/w, about 3.5% w/w, about 4% w/w, about 4.5% w/w or about 5% w/w of the composition.

In another embodiment, any of the pharmaceutical compositions described herein is an aqueous suspension for nasal administration to a human, comprising 0.025% w/w mometasone furoate, about 0.665% w/w of olopatadine hydrochloride and a de-clogging agent in an amount at a concentration of about 0.05% w/w to about 1% w/w, about 0.1% w/w to about 1% w/w, about 1% w/w to about 1.5% w/w, about 1.5% w/w to about 2.5% w/w, about 2.5% w/w to about 3% w/w, about 3% w/w to about 3.5% w/w, about 3.5% w/w to about 4% w/w or about 4% w/w to about 5% w/w of the composition.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.05% w/w to about 5% w/w of glycerol.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.1% w/w to about 5% w/w of glycerol.

In yet another embodiment, any of the pharmaceutical compositions described herein is an aqueous suspension for nasal administration to a human, comprising about 0.025% w/w mometasone furoate, about 0.665% w/w olopatadine hydrochloride and about 0.1% w/w to about 3% w/w of glycerol.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 2% w/w of glycerol.

In yet another embodiment, the pharmaceutical composition described herein is an aqueous suspension for nasal administration to a human, comprising about 0.025% w/w mometasone furoate, about 0.665% w/w olopatadine hydrochloride and about 0.01% to about 1% w/w (such as about 0.1% w/w to about 1% w/w) of glycerol.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w of glycerol.

In another embodiment, the pharmaceutical composition described herein is an aqueous suspension for nasal administration to a human, comprising about 0.025% w/w mometasone furoate, about 0.665% w/w olopatadine hydrochloride and about 0.05% w/w to about 5% w/w of a de-clogging agent which controls the clogging of a nasal spray actuator and/or dip tube (for example, for at least about 5 days) through which the pharmaceutical composition is delivered.

In yet another embodiment, the pharmaceutical composition described herein is an aqueous suspension for nasal administration to a human, comprising about 0.025% w/w mometasone furoate, about 0.665% w/w olopatadine hydrochloride and about 0.05% w/w to about 5% w/w of a de-clogging agent which controls the clogging of a nasal spray actuator and/or dip tube (through which the pharmaceutical composition is delivered) for at least about 10 days, for at least about 15 days, for at least about 20 days, at least about 25 days, for at least about 30 days.

In one embodiment, the control of clogging of the nasal spray actuator and/or dip tube up to 30 days is observed even when the dispensing device remains open without a dust cap fitted on it, or the dust cap improperly fitted on the dispensing device.

In yet another embodiment, the pharmaceutical composition described herein is an aqueous suspension for nasal administration to a human, comprising about 0.025% w/w mometasone furoate, about 0.665% w/w olopatadine hydrochloride and about 0.05% w/w to about 5% w/w of a de-clogging agent which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 5% w/w of a de-clogging agent which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 5% w/w of a de-clogging agent which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 3% w/w of a de-clogging agent which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 3% w/w of a de-clogging agent which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 1% w/w of a de-clogging agent which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 1% w/w of a de-clogging agent which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.05% w/w to about 5% w/w of glycerol which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.05% w/w to about 5% w/w of glycerol which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 5% w/w of glycerol which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 5% w/w of glycerol which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 3% w/w of glycerol which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 3% w/w of glycerol which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 1% w/w of glycerol which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w to about 1% w/w of glycerol which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the pharmaceutical composition described herein is an aqueous suspension for nasal administration to a human, comprising about 0.025% w/w mometasone furoate, about 0.665% w/w olopatadine hydrochloride and about 0.1% w/w of glycerol which controls the clogging of a nasal spray actuator and/or dip tube for at least about 5 days, for at least about 10 days, for at least about 15 days, for at least about 20 days, at least about 25 days, for at least about 30 days.

In yet another embodiment, the pharmaceutical composition described herein is an aqueous suspension for nasal administration to a human, comprising about 0.025% w/w mometasone furoate, about 0.665% w/w olopatadine hydrochloride and about 0.1% w/w of glycerol which controls the clogging of a nasal spray actuator and/or dip tube for about 5 days to about 30 days, for about 5 days to about 25 days, for about 5 days to about 20 days, for about 5 days to about 15 days, for about 5 days to about 10 days.

In another embodiment, the de-clogging agent may be present at a concentration of about 0.05% w/w to about 1% w/w, about 0.1% w/w to about 2% w/w, about 1% w/w to about 3% w/w, about 1.5% w/w to about 4% w/w, about 2.5% w/w to about 4% w/w, about 3% w/w to about 3.5% w/w, about 3.5% w/w to about 4% w/w or about 4% w/w to about 5% w/w of the composition.

In another embodiment, the de-clogging agent is glycerol (or glycerin) present at a concentration of about 0.05% w/w to about 1% w/w, about 0.1% w/w to about 2% w/w, about 0.1% w/w to about 3% w/w, about 1% w/w to about 3% w/w, about 1.5% w/w to about 4% w/w, about 2.5% w/w to about 4% w/w, about 3% w/w to about 3.5% w/w, about 3.5% w/w to about 4% w/w, or about 4% w/w to about 5% w/w of the composition.

In another embodiment, the de-clogging agent is glycerol (or glycerin) present at a concentration of between about 0.1% w/w to about 5% w/w.

In another embodiment, the de-clogging agent is glycerol (or glycerin) present at a concentration of about 0.05% w/w, about 0.06% w/w, about 0.07% w/w, about 0.08% w/w, about 0.09% w/w, about 0.1% w/w, about 0.125% w/w, about 0.15% w/w, about 0.17% w/w, about 0.18% w/w, about 0.19% w/w, about 0.2% w/w, 0.3% w/w, 0.4% w/w, 0.5% w/w, 0.6% w/w, 0.7% w/w, 0.8% w/w, 0.9% w/w, 1% w/w, 1.2% w/w, 1.3% w/w, 1.4% w/w, 1.5% w/w, 1.6% w/w, 1.8% w/w, 2% w/w, 2.5% w/w or 3% w/w of the composition.

In another embodiment, the de-clogging agent is sorbitol present at a concentration of about 0.05% w/w, about 0.1% w/w, 0.2% w/w, 0.3% w/w, 0.4% w/w, 0.5% w/w, 0.6% w/w, 0.7% w/w, 0.8% w/w, 0.9% w/w, 1% w/w, 1.2% w/w, 1.3% w/w, 1.4% w/w, 1.5% w/w, 1.6% w/w, 1.8% w/w, 2% w/w, 2.5% w/w or 3% w/w of the composition.

In another embodiment, the de-clogging agent is sorbitol present at a concentration of about 0.05% w/w to about 1% w/w, about 0.1% w/w to about 2% w/w, about 0.1% w/w to about 3% w/w, about 1% w/w to about 3% w/w, about 1.5% w/w to about 4% w/w, about 2.5% w/w to about 4% w/w, about 3% w/w to about 3.5% w/w, about 3.5% w/w to about 4% w/w or about 4% w/w to about 5% w/w of the composition.

In another embodiment, the de-clogging agent is mannitol present at a concentration of about 0.05% w/w to about 1% w/w, about 0.1% w/w to about 2% w/w, about 1% w/w to about 3% w/w, about 1.5% w/w to about 4% w/w, about 2.5% w/w to about 4% w/w, about 3% w/w to about 3.5% w/w, about 3.5% w/w to about 4% w/w or about 4% w/w to about 5% w/w of the composition.

In another embodiment, the de-clogging agent is mannitol present at a concentration of about 0.05% w/w, about 0.1% w/w, 0.2% w/w, 0.3% w/w, 0.4% w/w, 0.5% w/w, 0.6% w/w, 0.7% w/w, 0.8% w/w, 0.9% w/w, 1% w/w, 1.2% w/w, 1.3% w/w, 1.4% w/w, 1.5% w/w, 1.6% w/w, 1.8% w/w, 2% w/w, 2.5% w/w or 3% w/w of the composition.

In another embodiment, the de-clogging agent is propylene glycol present at a concentration of about 0.05% w/w to about 1% w/w, about 0.1% w/w to about 2% w/w, about 1% w/w to about 3% w/w, about 1.5% w/w to about 4% w/w, about 2.5% w/w to about 4% w/w, about 3% w/w to about 3.5% w/w, about 3.5% w/w to about 4% w/w or about 4% w/w to about 5% w/w of the composition.

In another embodiment, the de-clogging agent is propylene glycol present at a concentration of about 0.05% w/w, about 0.1% w/w, 0.2% w/w, 0.3% w/w, 0.4% w/w, 0.5% w/w, 0.6% w/w, 0.7% w/w, 0.8% w/w, 0.9% w/w, 1% w/w, 1.2% w/w, 1.3% w/w, 1.4% w/w, 1.5% w/w, 1.6% w/w, 1.8% w/w, 2% w/w, 2.5% w/w or 3% w/w of the composition In another embodiment, the de-clogging agent is polyethylene glycol present at a concentration of about 0.05% w/w to about 1% w/w, about 0.1% w/w to about 2% w/w, about 1% w/w to about 3% w/w, about 1.5% w/w to about 4% w/, about 2.5% w/w to about 4% w/w, about 3% w/w to about 3.5% w/w, about 3.5% w/w to about 4% w/w or about 4% w/w to about 5% w/w of the composition.

In another embodiment, the de-clogging agent is polyethylene glycol present at a concentration of about 0.05% w/w, about 0.1% w/w, 0.2% w/w, 0.3% w/w, 0.4% w/w, 0.5% w/w, 0.6% w/w, 0.7% w/w, 0.8% w/w, 0.9% w/w, 1% w/w, 1.2% w/w, 1.3% w/w, 1.4% w/w, 1.5% w/w, 1.6% w/w, 1.8% w/w, 2% w/w, 2.5% w/w or 3% w/w of the composition In another embodiment, any of the pharmaceutical compositions described herein is an aqueous suspension for nasal administration to a human, comprising about 0.025% w/w to about 0.05% w/w mometasone furoate, about 0.6% w/w to about 0.7% w/w olopatadine hydrochloride, about 0.5% w/w to about 0.7% w/w carboxymethylcellulose sodium and about 0.1 w/w glycerol.

In another embodiment, any of the pharmaceutical compositions described herein is an aqueous suspension for nasal administration to a human, comprising about 0.025% w/w mometasone furoate, about 0.665% w/w olopatadine hydrochloride, about 0.67% w/w carboxymethylcellulose sodium and about 0.1% w/w glycerol.

It will also be appreciated to the skilled artisan that in order to improve the physical properties, appearance, and/or smell of the compositions of the present invention, one or more further pharmaceutically acceptable excipients may be added as desired. Suitable pharmaceutical acceptable excipients include, but are not limited to, chelating agents, preservatives, buffers, surfactants, isotonicity agents, taste masking agents, antioxidants, humectants, pH adjusting agents, and any combination of any of the foregoing.

Suitable surfactants which may be used for preparing aqueous nasal spray composition may include, e.g., one or more of anionic, cationic, non-ionic or zwitterionic surfactants. Examples of suitable surfactants which can be employed in the aqueous nasal spray suspension may be selected from, but are not limited to, polyethoxylated sorbitan derivatives such as polysorbates, their ether ethoxylates, produced by reaction of sorbitan esters with ethylene oxide, polyoxyethylene alkyl phenol, polyoxyethylene cetyl ether, polyoxyethylene alkyl-aryl ether, polyoxyethylene monolaurate, polyoxyethylene vegetable oil, polyoxyethylene sorbitan monolaurate, polyoxyethylene esters or mixed fatty and resin acids, polyoxyethylene sorbitol lanolin derivative, polyoxyethylene tridecylether, polyoxyethylene sorbitan esters of mixed fatty and resin acids, polyoxyethylene sorbitan monostearate, polyoxyethylene sorbitan monooleate, polyoxyethylene monostearate, polyoxyethylene stearyl ether, polyoxyethylene oleyl ether, polyoxyethylene tridecyl ether, polyoxyethylene fatty alcohol, polyoxyethylene alkyl amine, polyoxyethylene glycol monopalmitate, polyoxyethylene sorbitan monopalmitate, polyoxyethylene cetyl ether, polyoxyethylene oxypropylene stearate, polyoxyethylene lauryl ether, polyoxyethylene lanolin derivative, sodium oleate, quaternary ammonium derivative, potassium oleate, N-cetyl N-ethyl morpholinium ethosulfate, sodium lauryl sulfate or mixtures thereof. Preferred surfactants are polyethoxylated sorbitan derivatives (such as polysorbate 80). The amount of surfactant may range from about 0.001% to about 1% w/w relative to the total weight of the composition.

In order to improve the ability of the aqueous nasal spray suspension to be tolerated on administration to the nasal mucous membrane, it is advantageous to formulate it as isotonic. The osmolality can be set by variation of the amounts of the substances present in the aqueous nasal spray suspension besides the active agents, and/or by addition of an isotonicity agent, preferably a physiologically tolerated salt, such as, for example, sodium chloride or potassium chloride. The amount of isotonicity agent may range from about 0.001% to about 1% w/w relative to the total weight of the composition.

Examples of suitable preservatives which can be employed in the aqueous nasal spray suspensions described herein include, but are not limited to, benzyl alcohol, quaternary ammonium halides, phenylcarbinol, thimerosal, and disodium edetate. Quaternary ammonium halide preservatives are preferred. Suitable quaternary ammonium halide preservatives include, e.g., polyquaternium-1 and benzalkonium halides. Preferred benzalkonium halides include benzalkonium chloride and benzalkonium bromide. The amount of the preservative may range from about 0.005 to about 0.2% w/w relative to the total weight of the composition. Preferably, the preservative is present at a concentration of about 0.02% w/w relative to the total weight of the composition.

Examples of suitable chelating agents which can be employed in the aqueous nasal spray suspensions described herein include, but are not limited to, edetate disodium (EDTA), edetate trisodium, edetate tetrasodium, and diethyleneamine pentaacetate, preferably EDTA. The amount of the chelating agent present in the aqueous nasal spray suspensions described herein may range from about 0.0002% w/w to about 0.5% w/w relative to the total weight of the composition.

Examples of suitable buffers which can be employed in the aqueous nasal spray suspensions described herein include, but are not limited to, citric acid, acetic acid, fumaric acid, hydrochloric acid, malic acid, nitric acid, phosphoric acid, propionic acid, sulfuric acid, tartaric acid, phosphate salts (e.g., dibasic sodium phosphate, such as dibasic sodium phosphate heptahydrate), or combinations thereof. The suspensions of the present invention may comprise an amount of a buffer sufficient to maintain the pH of the composition to from about 3 to about 6.Preferably, the amount of buffer ranges from about 0.005% to about 2% w/w relative to the total weight of the composition.

Examples of suitable sweetener/taste masking agents which can be employed in the aqueous nasal spray suspensions described herein include, but are not limited to, sucralose, thaumatin, sucrose, saccharin (including salt forms such as sodium and calcium salts), fructose, glucose, dextrose, corn syrup, aspartame, acesulfame-K, xylitol, sorbitol, erythritol, ammonium glycyrrhizinate, neotame, mannitol, eucalyptus oil, camphor, and natural or artificial flavors or flavoring agents (for example menthol, mints, vanilla, orange, etc.), or combinations of two or more of such agents. A preferred taste masking agent is sucralose. The amount of the sweetener/taste masking agent present in the aqueous nasal spray suspension may range from about 0.01% to about 1% w/w relative to the total weight of the composition.

Examples of suitable antioxidants which can be employed in the aqueous nasal spray suspensions described herein include, but are not limited to, ascorbic acid, alpha-tocopherol (vitamin-E), butylated hydroxyanisole, butylated hydroxytoluene, glutathione, and any combination of any of the foregoing. The amount of the antioxidants present in the aqueous nasal spray composition may range from about 0.0002% w/w to about 0.5% w/w relative to the total weight of the composition.

Suitable pH adjusting agents include, but are not limited to, sodium hydroxide and hydrochloric acid.

An aqueous suspension for nasal administration as described herein may have a pH of between about 3.3 and about 4.1, or between about 3.5 and about 3.9.

The osmolality of any of the compositions described herein may range between about 200 mOsm/kg and about 400 mOsm/kg, or about 250 mOsm/kg and about 350 mOsm/kg. The viscosity of any of the compositions described herein may be about 10 cps to about 200 cps, such as from about 20 cps to about 150 cps or from about 20 cps to about 120 cps. The viscosity can be determined by various known instruments such as a Dynamic stress rheometer or Brookfield viscometer. In a preferred embodiment, the viscosity is determined by a Brookfield viscometer by measuring torque transmission through a sample using a rotating spindle.

In yet another aspect, any of the compositions described herein may be in the form of a suspension comprising particles of mometasone, an ester thereof, (such as mometasone furoate) or a salt thereof, wherein the particles have a mean particle size in the range of from about 1 μm to about 20 μm, such as from about 1 μm to about 15 μm. In one embodiment, the suspension the particles have a mean particle size of less than 15 μm when determined by a microscopy technique.

In yet another aspect, any of the compositions described herein, when delivered in a dispensing device exhibit a spray pattern having a longest axis of about 15-75 mm, a shortest axis of about 10-65 mm, and an ellipticity of about 1-2.

In yet another embodiment, any of the compositions described herein is an aqueous suspension for nasal administration to a human, comprising mometasone furoate monohydrate, olopatadine hydrochloride and a de-clogging agent comprising glycerol (or glycerin) at a concentration of at least about 0.1% w/w of the composition, wherein the composition has a pH between about 3.5 and about 4.1.

In yet another embodiment, any of the compositions described herein is an aqueous suspension for nasal administration to a human, comprising mometasone furoate monohydrate, olopatadine hydrochloride and a de-clogging agent comprising glycerol (or glycerin) at a concentration of at least about 0.1% w/w of the composition.

In yet another embodiment, any of the compositions described herein is an aqueous suspension for nasal administration to a human, comprising mometasone furoate monohydrate, olopatadine hydrochloride and a de-clogging agent comprising glycerol (or glycerin) at a concentration between about 0.1% w/w to about 5% w/w of the composition.

In yet another embodiment, any of the compositions described herein is an aqueous suspension for nasal administration to a human, comprising mometasone furoate monohydrate, olopatadine hydrochloride and a de-clogging agent comprising sorbitol at a concentration of at least about 0.1% w/w of the composition.

In yet another embodiment, any of the compositions described herein is an aqueous suspension for nasal administration to a human, comprising mometasone furoate monohydrate, olopatadine hydrochloride and a de-clogging agent comprising polyethylene glycol at a concentration of at least about 0.1% w/w of the composition.

In yet another embodiment, any of the compositions described herein further comprise:

a chelating agent in an amount of about 0.0002 to about 0.5% w/w;

an isotonicity agent of about 0.001% to about 1% w/w;

a surfactant in an amount of about 0.001% to about 1% w/w;

preservative in an amount of about 0.005 to about 0.2% w/w; and a buffer in an amount of about 0.005% to about 1% w/w.

In yet another embodiment, any of the compositions described herein comprise, in addition to the olopatadine (e.g. olopatadine hydrochloride) and mometasone furoate, (i) about 0.1% glycerol, (ii) 0.5% w/w carboxymethyl cellulose sodium, (iii) about 1.2% w/w of a mixture of microcrystalline cellulose and carboxymethyl cellulose sodium, (iv) about 0.02% w/w benzalkonium chloride, (v) about 0.41% w/w sodium chloride, (vi) about 0.01% w/w disodium edetate, (vii) about 0.94% w/w dibasic sodium phosphate, and (viii) about 0.01% polysorbate 80.

In yet another embodiment, any of the compositions described herein is an aqueous suspension composition for nasal administration to a human, wherein the composition comprises (1) about 0.025% w/w mometasone furoate monohydrate, (2) about 0.665% w/w olopatadine hydrochloride, (3) a de-clogging agent selected from about 0.1% w/w of glycerol (or glycerin), about 0.1% w/w of sorbitol, about 0.1% w/w polyethylene glycol and about 0.1% w/w of mannitol, (4) a hydrocolloid selected from about 0.3% w/w of xanthan gum and about 0.67% w/w carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

In yet another embodiment, any of the compositions described herein is an aqueous suspension composition for nasal administration to a human, wherein the composition comprises (1) about 0.025% w/w mometasone furoate monohydrate, (2) about 0.665% w/w olopatadine hydrochloride, (3) a de-clogging agent selected from about 0.1% w/w glycerol (or glycerin), about 0.1% w/w sorbitol, about 0.1% w/w polyethylene glycol and about 0.1% w/w mannitol, (4) a hydrocolloid selected from about 0.3% w/w xanthan gum and about 0.5% w/w carboxymethyl cellulose sodium, (5) about 1% w/w to about 1.2% w/w of a mixture of microcrystalline cellulose and carboxymethyl cellulose sodium, (6) about 0.02% w/w benzalkonium chloride, (7) about 0.41% w/w sodium chloride, (8) about 0.01% w/w di-sodium edetate, (9) about 0.94% w/w sodium phosphate heptahydrate, and (10) about 0.01% polysorbate 80.

In a further embodiment, the dispensing devices described herein contain any of the pharmaceutical compositions described herein in the form of a kit with a package insert containing instructions about use of the pharmaceutical composition.

In one embodiment, the composition when stored for up to 12 months at 25±2° C. and 60%±5% relative humidity in the dispensing device contains has one or more of the following properties:

(i) the composition contains not more than 1% of total impurities (after storage);

(ii) the composition contains not more than 0.5% of DMC (after storage);

(iii) the composition contains not more than 0.5% of DMCF (after storage);

(iv) the composition contains not more than 0.5% of a-hydroxy olopatadine (after storage);

(v) the composition contains not more than 0.5% of olopatadine E-isomer (after storage);

(vi) the composition contains not more than 0.5% of Olopatadine Related Compound B (after storage); and/or (vii) the composition contains not more than 0.2% of other impurities of olopatadine (after storage).

(viii) the composition contains not more than 8-DM (after storage).

In a further embodiment, the pharmaceutical compositions described herein, when dispensed from a dispensing device described herein, can provide a spray pattern having a longest axis of about 15-75 mm, a shortest axis of about 10-65 mm, and an ellipticity of about 1-2. The spray pattern can be determined by various known techniques, such as with an ADSA with NSPUA set up (Innova System) and the spray droplet size distribution can be determined by various known techniques such as with a Malvern Spraytec with NSPUA set up (Innova System).

The following describes a typical procedure for characterizing droplet size distribution of the spray. The sprayer is loaded with a composition as described herein and primed by an actuating pump via an actuator until a fine mist appears out of the nozzle of the sprayer. A commercially available laser diffraction instrument is arranged so that the nozzle is about 3 cm or about 6 cm below the laser beam of the laser diffraction instrument. The pump is actuated with an actuator using a constant force. The resulting spray of the composition crosses the laser beam. Data are collected for $D_{10}$, $D_{50}$, $D_{90}$, and SPAN ($D_{90}$-$D_{10}$/$D_{50}$). The average values for each of these parameters for three sprays are calculated.

In a further embodiment, the pharmaceutical compositions described herein, when dispensed from the dispensing device, can provide the following droplet size distribution:

$D_{10}$: about 5 μm-35 μm, more preferably about 10 μm-30 μm, and most preferably about 10 μm-25 μm at 3 cm distance, and about 5 μm-40 μm, more preferably about 10 μm-35 μm, and most preferably about 10-30 μm 6 cm distance;

$D_{50}$: about 10 μm-90 μm, more preferably about 20 μm-80 μm, and most preferably about 25 μm-75 μm at 3 cm or 6 cm distance;

$D_{90}$: about 30 μm-180 μm, more preferably about 40 μm-170 μm, and most preferably about 50 μm-160 μm at 3 cm or 6 cm distance;

SPAN: not more than about 4, more preferably about not more than about 3, such as about 2-3;

where $D_{10}$ is the droplet size distribution of 10% of the droplets, $D_{50}$ is the droplet size distribution of 50% of the droplets, $D_{90}$ is the droplet size distribution of 90% of the droplets; SPAN is the ratio of ($D_{90}$-$D_{10}$)/$D_{50}$. In a further embodiment, the pharmaceutical compositions described herein, when dispensed from the dispensing device, can provide a delivered dose or spray content uniformity collected at the beginning of unit life and at the label claim number of metered sprays, from each of 10 separate containers, meeting the following acceptance criteria: not more than 2 of the 20 doses are outside the range of about 80% to about 120% of the label claim, and none are outside the range of about 75% to about 125% of the label claim, while the mean for each of the beginning and end doses falls within the range of about 85% to about 115% of the label claim. If 3-6 doses of the 20 doses collected are outside of about 80% to about 120% of the label claim, but none are outside of about 75% to about 125% of the label claim, and the means for each of the beginning and end doses fall within about 85% to about 115% of label claim, select 20 additional containers for second-tier testing. For second-tier testing, the requirements are met if not more than 6 of the 60 doses collected are outside the range of about 80% to about 120% of the label claim, none are outside the range of about 75% to about 125% of the label claim, and the means for each of the beginning and end doses fall within the range of about 85% to about 115% of the label claim.

To ensure reproducible in-vitro dose collection, a mechanical means of actuating the pump assembly may be employed to deliver doses for collection. The mechanical actuation procedure should have adequate controls for the critical mechanical actuation parameters (e.g., actuation force, actuation speed, stroke length, rest periods, etc.). The test is performed on units that have been primed according to the patient-use instructions. The test unit should be actuated in a vertical or near vertical, valve-up, position. The two doses collected at the beginning and end of the container life should be the dose immediately following priming and the dose corresponding to the last label claim number of doses from the container.

The delivered dose or spray content uniformity can be determined by delivering the dose into a suitable container (e.g., scintillation vial) in which quantitative transfer from the container under test can be accomplished. A validated analytical method is employed to determine the amount of drug in each delivered dose, and data are reported.

EXAMPLES

Examples 1 & 2

| Sr. No | Material | Example 1 % w/w | Example 2 % w/w |
|---|---|---|---|
| 1 | Mometasone furoate | 0.025 | 0.025 |
| 2 | Olopatadine hydrochloride | 0.665 | 0.665 |
| 3 | Mixture of microcrystalline cellulose and carboxymethylcellulose sodium (Avicel RC-591) | 1.20 | 1.20 |
| 4 | Carboxymethylcellulose sodium | 0.50 | 0.50 |
| 5 | Glycerin | — | 0.1 |
| 6 | Sodium chloride | 0.41 | 0.41 |
| 7 | Edetate disodium | 0.01 | 0.01 |
| 8 | Dibasic sodium phosphate | 0.940 | 0.940 |
| 9 | Polysorbate 80 | 0.01 | 0.01 |
| 10 | Benzalkonium Chloride | 0.02 | 0.02 |
| 11 | Hydrochloric acid | q.s. to adjust pH | q.s. to adjust pH |
| 12 | Sodium hydroxide | q.s. to adjust pH | q.s. to adjust pH |
| 13 | Water for injection | q.s. to 100 | q.s. to 100 |

Manufacturing Procedure

For Example-1

1. A mixture of microcrystalline cellulose and carboxymethylcellulose sodium was added to water for injection with homogenization and allowed to hydrate.
2. Carboxymethylcellulose sodium was dispersed in water for injection and added to the product of step-1.
3. Dibasic sodium phosphate heptahydrate, sodium chloride, edetate disodium and olopatadine HCl were dissolved in water. The pH was adjusted to 2.8-3.2 with hydrochloric acid.
4. The product of step-3 was added to the product of step-1 with homogenization.

5. Polysorbate 80 was dissolved in water for injection. Mometasone furoate monohydrate was added and stirred to form a slurry.
6. The product of step-5 was added to the product of step-4 with homogenization.
7. Benzalkonium chloride was dissolved in water for injection.
8. The product of step-7 was added to the product of step-6 with homogenization.
9. The pH was checked and adjusted to 3.5-3.9 with HCls/NaOH and the total weight was adjusted with water for injection. The osmolality of the composition was about 250-350 mOsm/kg. The composition was subjected to stability studies at different conditions.

For Examples-2

1. A mixture of microcrystalline cellulose and carboxymethylcellulose sodium was added to water for injection with homogenization and allowed to hydrate.
2. Carboxymethylcellulose sodium was dispersed in water for injection and added to the product of step-1.
3. Dibasic sodium phosphate heptahydrate, sodium chloride, edetate disodium and olopatadine HCl were dissolved in water. The pH was adjusted to 2.8-3.2 with hydrochloric acid.
4. The product of step-3 was added to the product of step-1 with homogenization.
5. Polysorbate 80 was dissolved in water for injection. Mometasone furoate monohydrate was added and stirred to form a slurry.
6. The product of step-5 was added to the product of step-4 with homogenization.
7. Benzalkonium chloride was dissolved in water for injection.
8. The product of step-7 was added to the product of step-6 with homogenization.
9. Glycerol was dissolved in water
10. The product of step-9 was added to the product of step-3 with homogenization.
11. The pH was checked and adjusted to 3.5-3.9 with HCl/NaOH and the total weight was adjusted with water for injection. The osmolality of the composition was about 250-350 mOsm/kg. The composition was subjected to stability studies at different conditions.

The formulation of Examples 1 and 2 were tested for clogging problem in a dispensing device.

Pack size: 240 dose

Study duration: 30 days

| Formulation Details | Pack Details (240 MD) | Sample Details - Daily 8 Spray/ No. of samples | |
|---|---|---|---|
| | | With cap | Without cap |
| Example 1 | 30 ml HDPE bottle + Pump + Actuator + with and without cap | 50 nos. | 50 nos. |
| Example 2- Batch 1 | 30 ml HDPE bottle + Pump + Actuator + without cap | — | 50 nos. |
| Example 2- Batch 2 | 30 ml HDPE bottle + Pump + Actuator + without cap | — | 50 nos. |
| Example 2- Batch 3 | 30 ml HDPE bottle + Pump + Actuator + without cap | — | 50 nos. |

3 Batches were manufactured using the formulation of example 2.

Study Procedure

A) Sample Without Cap

1. The study was initiated with the bottles in open condition (i.e., without putting a cap after spraying) and, as a control, with a cap (a cap was placed on the actuator after spraying). The study was continued for 30 days at ambient temperature.
2. Before initiation of the study, all actuators were primed 6 times.
3. Each bottle was sprayed daily for 8 spray for 30 days.
4. The spray pattern was observed visually during spraying.
5. Clogging of each actuator was observed during spraying.
6. If clogging was observed, the bottle was kept aside and on the next day, the same procedure was performed to check whether the actuator was still clogged or not.

7. If any clogging was observed (partial or complete), those bottles were kept aside and the observation was recorded.

B) Sample With Cap

1. The procedure described above was followed for the sample with cap study.
2. The cap was placed on the actuator and the instructions below were followed
   a) Wipe the spray pump tip with a clean dry tissue or cloth.
   b) Hold the spray pump unit and push the dust cap back on the spray pump tip of the bottle.

Actuator and/or Dip Tube Clogging Study—Visual Observations and Conclusion

| Sr. No | Sample Qty. | Batch details | Details summary and observation |
|---|---|---|---|
| 1 | 50 nos. | Ex 1 - with cap | No clogging seen. |
| 2 | 50 nos. | Ex 1- without cap | 11 actuators clogged - 8 opened on the next day, 3 actuators completely clogged. |
| 3 | 50 nos. | Ex 2- batch 1 without cap | 1 bottle actuator clogged but opened on next day. No further clogging seen. |
| 4 | 50 nos. | Ex 2- batch 2 without cap | No clogging seen. |
| 5 | 50 nos. | Ex 2- batch 3 without cap | No clogging seen. |

As can be seen, a formulation containing 0.1% w/w glycerol (or glycerin) controls an actuator from clogging during 30 days use.

2. Stability Data for Example 2

A) 25° C.±2° C. and 60% RH±5% RH

| Tests | Specifications | Initial | 1 M | 3 M | 6 M |
|---|---|---|---|---|---|
| Description | Physical appearance | Complies | Complies | Complies | Complies |
| | Assay (by HPLC) | | | | |
| a) Mometasone Furoate | 90.0%-110.0% of the label claim. | 103.3 | 100.7 | 101.2 | 102.8 |
| b) Olopatadine | 90.0%-110.0% of the label claim. | 100.2 | 99.7 | 100.8 | 100.7 |
| | Related substances for Mometasone Furoate by HPLC | | | | |
| Impurity 8DM | Not more than 0.5% | ND | ND | ND | ND |
| Impurity DMC | Not more than 0.5% | ND | ND | ND | ND |
| Impurity DMCF | Not more than 0.5% | ND | ND | ND | 0.06 |
| Any other impurity | Not more than 0.5% | ND | ND | ND | ND |
| Total impurities | Not more than 1.0% | ND | ND | ND | 0.06 |
| | Related substances for Olopatadine HCl by HPLC | | | | |
| α Hydroxy Olopatadine | Not more than 0.5% | ND | ND | ND | BLOQ (0.005) |
| Olopatadine E-Isomer | Not more than 0.5% | 0.18 | 0.14 | 0.16 | 0.18 |
| Related Compound B | Not more than 0.5% | ND | 0.01 | ND | 0.04 |
| Olopatadine carbaldehyde (z) isomer | Not more than 0.2% | BLOQ | 0.03 | 0.08 | 0.02 |
| Any other impurity | Not more than 0.2% | 0.07 | 0.06 | 0.09 | 0.06 |

| Tests | Specifications | Initial | 1 M | 3 M | 6 M |
|---|---|---|---|---|---|
| Total impurities | Not more than 1.0% | 0.28 | 0.32 | 0.41 | 0.40 |

Droplet size Distribution by Laser diffraction

| | Parameters | Tip-to-laser Distance | | Tip-to-laser Distance | | | | | | | |
|---|---|---|---|---|---|---|---|---|---|---|---|
| | | 3 cm | 6 cm | 3 cm | 6 cm | 3 cm | 6 cm | 3 cm | 6 cm | 3 cm | 6 cm |
| A) At 3.0 cm distance | | 3 cm | 6 cm | | | | | | | | |
| B) At 6.0 cm distance | D 10 | 10-25 µm | 10-30 µm | 14.71 | 16.12 | 14.27 | 16.12 | 14.14 | 16.56 | 13.93 | 15.58 |
| C) At 3.0 cm distance | D 50 | 25-75 µm | 25-65 µm | 37.63 | 34.54 | 35.13 | 33.22 | 36.08 | 33.32 | 34.26 | 32.40 |
| % droplets <10 µm | D 90 | 65-155 µm | 50-145 µm | 94.03 | 73.29 | 87.21 | 66.43 | 90.46 | 67.61 | 84.19 | 63.84 |
| 10 units × 3 sprays (n = 30) | SPAN | NMT 3.0 | NMT 3.0 | 2.11 | 1.65 | 2.06 | 1.51 | 2.12 | 1.53 | 2.05 | 1.49 |
| | | Not more than 10.0% | | 2.60 | | 2.91 | | 3.50 | | 3.55 | |

B) 40° C.±2° C. and 75% RH±5% RH

| Tests | Specifications | Initial | 1 M | 3 M | 6M |
|---|---|---|---|---|---|
| Description | Physical appearance | Complies | Complies | Complies | Complies |
| | Assay (by HPLC) | | | | |
| a) Mometasone Furoate | 90.0%-110.0% of the label claim. | 103.3 | 101.7 | 100.4 | 104.8 |
| b) For Olopatadine | 90.0%-110.0% of the label claim. | 100.2 | 100.1 | 100.8 | 100.8 |
| | Related substances for Mometasone Furoate by HPLC | | | | |
| Impurity 8DM | Not more than 0.5% | ND | ND | ND | ND |
| Impurity DMC | Not more than 0.5% | ND | ND | ND | ND |
| Impurity DMCF | Not more than 0.5% | ND | ND | 0.17 | 0.38 |
| Any other impurity | Not more than 0.5% | ND | ND | ND | ND |
| Total impurities | Not more than 1.0% | ND | ND | 0.17 | 0.38 |
| | Related substances for Olopatadine HCl by HPLC | | | | |
| α Hydroxy Olopatadine | Not more than 0.5% | ND | ND | 0.01 | 0.01 |
| Olopatadine E-Isomer | Not more than 0.5% | 0.18 | 0.12 | 0.14 | 0.17 |
| Related Compound B | Not more than 0.5% | ND | BLOQ | 0.01 | 0.05 |
| Olopatadine carbaldehyde (z) isomer | Not more than 0.2% | BLOQ | 0.04 | 0.19 | 0.06 |

| Tests | Specifications | Initial | 1 M | 3 M | 6 M |
|---|---|---|---|---|---|
| Any other impurity | Not more than 0.2% | 0.17 | 0.06 | 0.08 | 0.06 |
| Total impurities | Not more than 1.0% | 0.28 | 0.31 | 0.53 | 0.47 |

Droplet size Distribution by Laser diffraction

| | Parameters | Tip-to-laser Distance | | Tip-to-laser Distance | | | | | | | |
|---|---|---|---|---|---|---|---|---|---|---|---|
| | | 3 cm | 6 cm | 3 cm | 6 cm | 3 cm | 6 cm | 3 cm | 6 cm | 3 cm | 6 cm |
| A) At 3.0 cm distance | | 3 cm | 6 cm | | | | | | | | |
| B) At 6.0 cm distance | $D_{10}$ | 10-25 µm | 10-30 µm | 14.71 | 16.12 | 14.13 | 16.41 | 13.45 | 15.95 | 13.30 | 15.80 |
| C) At 3.0 cm distance | $D_{50}$ | 25-75 µm | 25-65 µm | 37.63 | 34.54 | 34.61 | 33.41 | 33.02 | 33.33 | 32.12 | 32.33 |
| % droplets <10 µm | $D_{90}$ | 65-155 µm | 50-145 µm | 94.03 | 73.29 | 85.69 | 66.35 | 81.79 | 66.71 | 78.59 | 63.73 |
| 10 units × 3 sprays (n = 30) | SPAN | NMT 3.0 | NMT 3.0 | 2.11 | 1.65 | 2.07 | 1.49 | 2.07 | 1.53 | 2.03 | 1.48 |
| | | Not more than 10.0% | | 2.60 | | 2.92 | | 4.12 | | 4.32 | |

We claim:

1. A nasal spray device comprising a container and a dispenser head, wherein the dispenser head comprises a pump, a dip tube, an actuator, and a dispensing orifice, the container includes a pharmaceutical composition, wherein (a) the composition is in the form of an aqueous suspension suitable for nasal administration, and (b) the composition comprises mometasone furoate in an amount of about 0.025% w/w in particulate form, olopatadine hydrochloride in an amount of about 0.665% w/w in dissolved form, and about 0.05% w/w to about 0.5% w/w of a de-clogging agent, wherein the de-clogging agent is glycerin.

2. The nasal spray device according to claim 1 wherein the amount of de-clogging agent in the pharmaceutical composition prevents the actuator and dip tube from clogging for at least 5 days.

3. The nasal spray device according to claim 1, wherein the amount of de-clogging agent in the pharmaceutical composition prevents the actuator and dip tube from clogging for at least 10 days.

4. The nasal spray device according to claim 1, wherein the amount of de-clogging agent in the pharmaceutical composition prevents the actuator and dip tube from clogging for about 20 days.

5. The nasal spray device according to claim 1, wherein the amount of de-clogging agent in the pharmaceutical composition prevents the actuator and dip tube from clogging for about 30 days.

6. The nasal spray device according to claim 1, wherein the amount of de-clogging agent in the pharmaceutical composition prevents the actuator and dip tube from clogging for about 5 days to about 30 days, when the dispensing device remains open without a dust cap.

7. The nasal spray device according to claim 1, wherein the mometasone furoate is present in the pharmaceutical composition as mometasone furoate monohydrate.

8. A method of treating a patient suffering from allergic rhinitis comprising administering through the nasal spray device of claim 1 an effective amount of the pharmaceutical composition to the patient.

9. The nasal spray device according to claim 1, wherein the pharmaceutical composition further comprises a hydrocolloid in an amount of about 0.3% w/w to about 3% w/w.

10. The nasal spray device according to claim 9, wherein the hydrocolloid is selected from carboxymethylcellulose sodium and xanthan gum.

11. The nasal spray device according to claim 9, wherein the pharmaceutical composition further comprises a chelating agent in an amount of about 0.0002 to about 0.5% w/w;

an isotonicity agent of about 0.001% to about 1% w/w;

a surfactant in an amount of about 0.001% to about 1% w/w;

preservative in an amount of about 0.005 to about 0.2% w/w; and a buffer in an amount of about 0.005% to about 1% w/w.

12. The nasal spray device according to claim 11, wherein the pharmaceutical composition comprises about 0.1% w/w glycerol, 0.5% w/w carboxymethyl cellulose sodium, about 1.2% w/w of a mixture of microcrystalline cellulose and carboxymethyl cellulose sodium, about 0.02% w/w benzalkonium chloride, about 0.41% w/w sodium chloride, about 0.01% w/w di-sodium edetate, about 0.94% w/w dibasic sodium phosphate, and about 0.01% polysorbate 80.

13. The nasal spray device according to claim 1, wherein the amount of de-clogging agent is 0.1% w/w.

14. The nasal spray device according to claim 1, wherein the nasal spray device is configured to dispense the pharmaceutical composition through the dip tube into the pump and then through the actuator fitted with the dispensing orifice.

* * * * *